United States Patent
Taylor

[11] 4,014,206
[45] Mar. 29, 1977

[54] APPARATUS AND METHOD FOR MONITORING AIR EMBOLI DURING EXTRACORPOREAL CIRCULATION

[75] Inventor: Bruce C. Taylor, Wayland, Mass.

[73] Assignee: Akron City Hospital, Akron, Ohio

[22] Filed: Mar. 31, 1975

[21] Appl. No.: 563,856

[52] U.S. Cl. .............................. 73/19; 128/214 E; 340/239 R
[51] Int. Cl.[2] ...................................... G01N 27/22
[58] Field of Search .............. 73/19, 23; 324/61 R, 324/65 R; 128/2 R, 2.05 R, 2.1 R, 2.05 E, 2.05 F, 214 E, DIG. 13; 340/237 R, 239 R

[56] References Cited
UNITED STATES PATENTS

| | | | |
|---|---|---|---|
| 3,155,901 | 11/1964 | Hanken | 324/61 R |
| 3,529,234 | 9/1970 | Keen | 73/19 |
| 3,898,637 | 8/1975 | Wolstenholme | 340/239 R |
| 3,903,478 | 9/1975 | Stuart et al. | 324/61 R |
| 3,935,876 | 2/1976 | Massie et al. | 340/237 R |

Primary Examiner—Richard C. Queisser
Assistant Examiner—Stephen A. Kreitman
Attorney, Agent, or Firm—Hamilton, Renner & Kenner

[57] ABSTRACT

Disclosed is a method and apparatus for detecting the presence of an embolism, such as air, during extracorporeal circulation in tubing carrying blood or other fluid such as would be present in the use of an artificial kidney machine. Electrodes are placed near the tubing to monitor the impedance thereof as well as the impedance of the fluid passing therethrough. An oscillator is attached to the electrodes and puts out a signal, the frequency of which is proportional to the basic impedance of the tubing and fluid. When an air bubble or the like passes the electrodes, the impedance will change causing a change in the frequency of the signal of the oscillator. The difference between the normal frequency and the changed frequency is indicative of the size of the embolism. Means are provided so that if a single embolism is large enough to cause damage to the patient or if a number of smaller emboli accumulate to the point of potentially causing damage to the patient, an alarm may be sounded or other remedial measures, such as system shutdown, could be taken. In addition, should the basic impedance of the fluid change, means are provided to prevent a false indication of an embolism.

7 Claims, 4 Drawing Figures

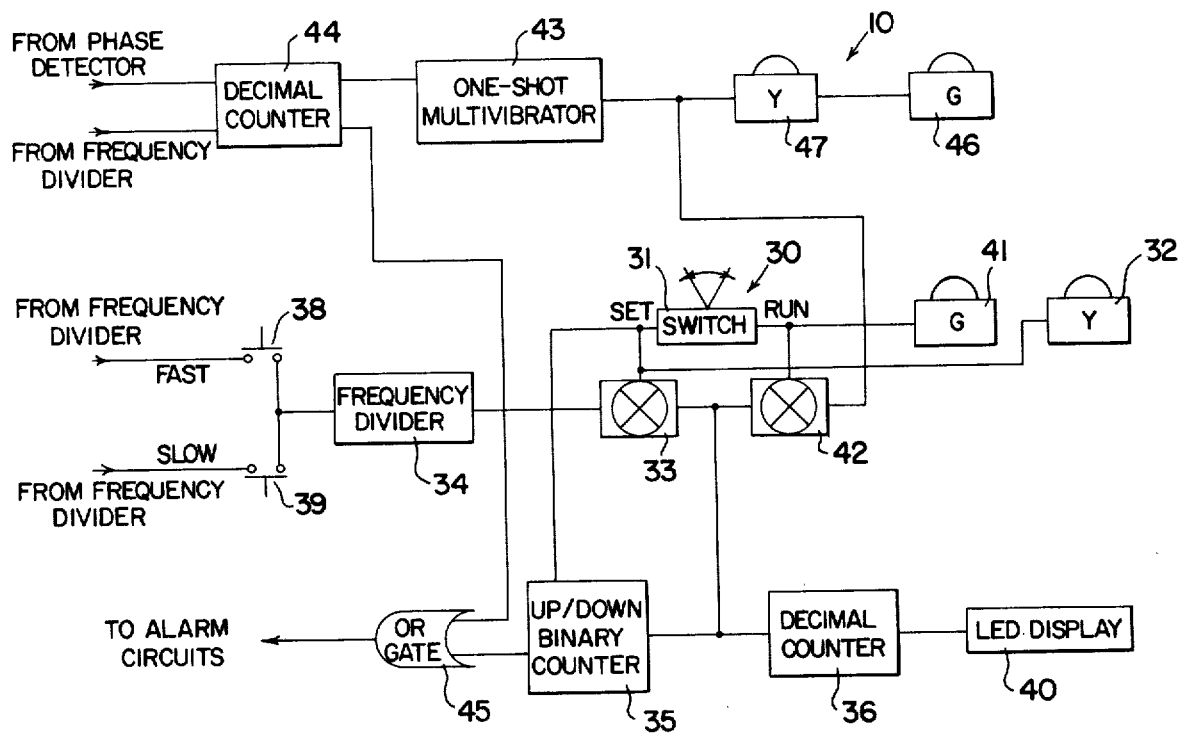
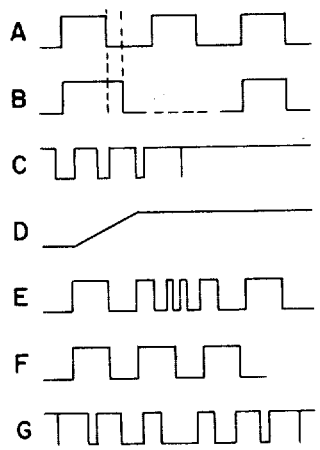
FIG. 3
FIG. 4

APPARATUS AND METHOD FOR MONITORING AIR EMBOLI DURING EXTRACORPOREAL CIRCULATION

BACKGROUND OF THE INVENTION

The present invention relates to an apparatus and method for monitoring air emboli, both macro and micro, present in blood during extracorporeal circulation. The danger of air emboli in pumped hemodialysis is an ever present and serious threat to the safety of patients who must use an artificial kidney machine. With the present increased use of A-V fistulas, there is danger of the presence of air emboli resulting from greater pumping pressures necessary to maintain an adequate flow of blood.

Not only is it difficult for the person who is operating the artificial kidney to monitor visually the flow of blood, to prevent entrapped air passing through the pump, the unit or its tubing from entering the patient's body, but also, due to the high cost and relative inconvenience of hospital hemodialysis, there has been an increased usage of home treatment units, where the dangers and effects of an air embolism are accordingly increased, primarily due to the lack of skilled operating personnel. Unfortunately, even in the hospital, as facilities are expanded to accommodate larger numbers of persons in need of hemodialysis, it is increasingly difficult for available skilled personnel to monitor all patients simultaneously and it would be economically impractical to provide trained personnel on a one-to-one basis with the patient. Lastly, although the operator may visually identify and remove macro air emboli, having a volume of approximately 0.5 ml, micro emboli, on the order of from 0.1 to 0.01 ml, may be expected to pass freely into the patient's body where a possible accummulation may occur before the body is able to remove the air.

Thus, the need for an apparatus or system to detect air entrapped in blood during extracorporeal circulation is manifest, primarily for the safety of the patient and secondarily to minimize the number of skilled personnel necessary to aid and assist the patients being treated. Such monitoring systems as are presently being used for the prevention of clinically significant air embolism during hemodialysis, have been designed to prevent the injection of a single, relatively large volume of air. The inability of existing monitors to detect micro air emboli is potentially hazardous and has been a basis for frequent criticism of these devices.

Several methods which have been used for the detection of air emboli in the extracorporeal tubing, a location where air is readily detectable and removable, utilize ultrasonic, photoelectric or electric sensors. These detectors are certainly better than no monitor, but are unable to perform satisfactorily under all conditions and to detect small volumes of air passage through the tubing. Criticisms of the photoelectric detectors have been reported as a result of false triggering occasioned by factors such as variations in color and optical density of the various fluids infused in the tubing during dialysis. Use of these detectors is also limited by the transparency and size of the various tubings available and their sensitivity, which often causes a false triggering with changes in the light intensity within a room.

Another disadvantage has been the necessity of disarming the sensor mechanism during various periods of treatment such as saline infusion, and, when the system has been disarmed, it must subsequently be reset and usually, with time-consuming adjustments.

Methods for monitoring electrical impedence of the blood lines also exist, however, these have undesirably required invasion of the blood stream with electrodes. At least one known system is able to detect air utilizing electrical impedance changes without direct contact with the flow of blood. By placing adjacent electrodes around the tubing, a capacitor is constructed whose dielectric is formed by the wall and the contents therein. Any fluid, conductive or nonconductive, increases the capacitance as its relative dielectric constant is much higher than that of air. Therefore, any air passing through the tubing as a bubble, induces between the electrodes a change in capacitance which is readily detected.

Notwithstanding the various devices which are available for monitoring air emboli and are presently being used, none has been found to possess the high sensitivity necessary to detect micro emboli without attendant, undesirable oversensitivity to external conditions, e.g., heat, light and movement. Moreover, frequent adjustments are often necessitated during operations of the devices or the equipment with which they are used to avoid erroneous indications. Finally, in order to avoid frequent responses to the micro emboli which some systems might be capable of detecting and which individually may not be harmful, the minimum size may be increased by the operator who then does not know the accumulated quantity of these emboli having passed into the patient within a given period of time.

SUMMARY OF THE INVENTION

It is therefore an object of the present invention to provide an apparatus and method for the detection of macro and micro air emboli in fluids circulating extracorporeally.

It is another object of the present invention to provide an apparatus and method for the detection of air emboli utilizing an AC coupled impedance technique which does not require direct contact with the fluid.

It is yet another object of the present invention to provide an apparatus which provides a change in capacitance upon detection of an air embolism, which in turn causes a change in frequency which ultimately may be used to trigger audio and visual alarms, to clamp the dialysis tubing thereby preventing passage of the air into the patient or to turn off the dialysis pump.

It is a further object of the present invention to provide an apparatus and method for the detection of air emboli which is sensitive to air entrapped in fluids, such as blood or saline, circulating through dialysis machines and the like, without requiring operator intervention and with a minimum of erroneous or false triggerings.

It is a further object of the present invention to provide an apparatus and method for the detection of not only a single volume of air, but also of the total, accumulated volume of micro air emboli which have passed through the apparatus in a given period of time or with the related volume of fluid passing therethrough.

It is yet another object of the present invention to provide an apparatus and method for the detection of air emboli on a volume basis which may be readily preset to trigger the necessary alarms in accordance with the total volume of air determined by the physician to be of potential danger to the patient.

It is yet a further object of the present invention to provide an apparatus and method for the detection of air emboli which requires little or no adjustment for the passage of various fluids through dialysis units and the like and which is insensitive to external conditions.

It is another object of the present invention to provide an apparatus and method for the detection of air emboli which is versatile and adaptable to a variety of applications including but not limited to hemodialysis, cardiopulmonary bypass and autotransfusion or any other situation where a volume of air occurring as macro or micro air emboli in extracorporeal circulation may present a potential hazard to the patient.

These and other objects of the present invention, together with the advantages thereof over existing and prior art forms which will become apparent from the following specifications, are accomplished by the means hereinafter specified.

In general, an apparatus for detecting at least one embolism contained in fluids during extracorporeal circulation in a tubing includes an oscillator which puts out a signal the frequency of which is proportional to the impedance of the fluid and tubing. A second oscillator monitors the fluid in the tubing to detect the presence of at least one embolism therein and provide an output signal the frequency of which is proportional to the tubing, fluid and the embolism. A detector circuit receives the outputs of the oscillators and provides an output signal, the duration of which is indicative of the difference between the frequencies of the oscillator outputs. When the output signal of the detector circuit is such that the presence of at least one embolism of sufficient size or volume to cause the patient a problem is detected, an alarm can be sounded and/or other remedial measures taken to prevent the embolism from reaching the patient.

BRIEF DESCRIPTION OF THE DRAWINGS

FIG. 3 is a block diagram showing the portion of the apparatus of the present invention not shown in FIG. 2, in particular, that portion which provides an actuation signal upon detection of a single embolism of damaging size, or a plurality of emboli which taken together could be damage to the patient.

FIG. 4 is a somewhat schematic representation of voltage waveforms at various points in the system and not necessarily to scale or coordinated in time, except as hereinafter specifically pointed out.

DESCRIPTION OF THE PREFERRED EMBODIMENT

Figure 1:
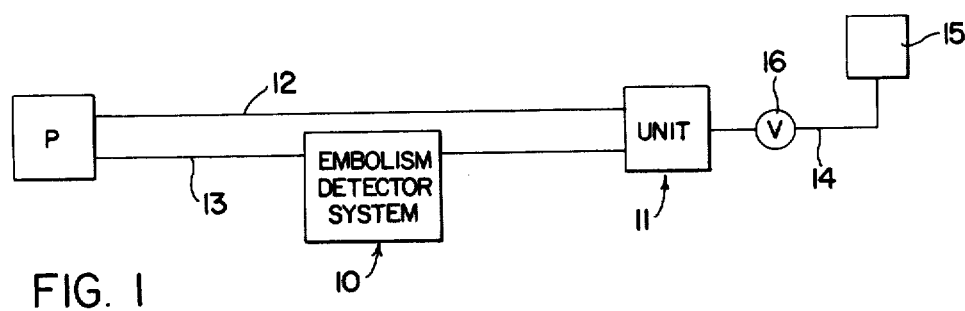
FIG. 1 is a schematic diagram depicting the patient, the apparatus of the present invention, the equipment for circulating fluid, and the system through which the fluid is circulated extracorporeally.

The embolism monitoring and detection apparatus of the present invention, indicated generally by the numeral 10, is depicted in FIG. 1 and in use will be positioned between the patient, indicated schematically by the letter P, and the return side of a unit such as an artificial kidney, referred to generally by the numeral 11. The unit 11, whether designed for hemodialysis, cardiopulmonary bypass, autotransfusion or the like, receives body fluid, such as blood, from the patient via an efferent line or tube 12. Likewise, the fluid to be returned to the patient is pumped from the unit 11, through an afferent tube 13, into the patient.

In addition to the tubes 12 and 13 for the extracorporeal circulation of the patient's blood through the unit 11, at least one other tube 14 is customarily provided to infuse saline from a source 15, to the patient in order to control hypovolemia. The flow of saline through tube 14 may be directly into the unit 11 and is customarily regulated via a valve 16. Although the saline may be introduced at another location, depending upon the operation of the unit 11 or the treatment selected by the physician, its introduction directly into the unit 11 has been depicted for purposes of simplification and clarity. Similarly, other fluids may be dispensed into or drawn from the unit 11 by additional tubes not shown, depending again upon the prescribed treatment of the patient.

Figure 2:
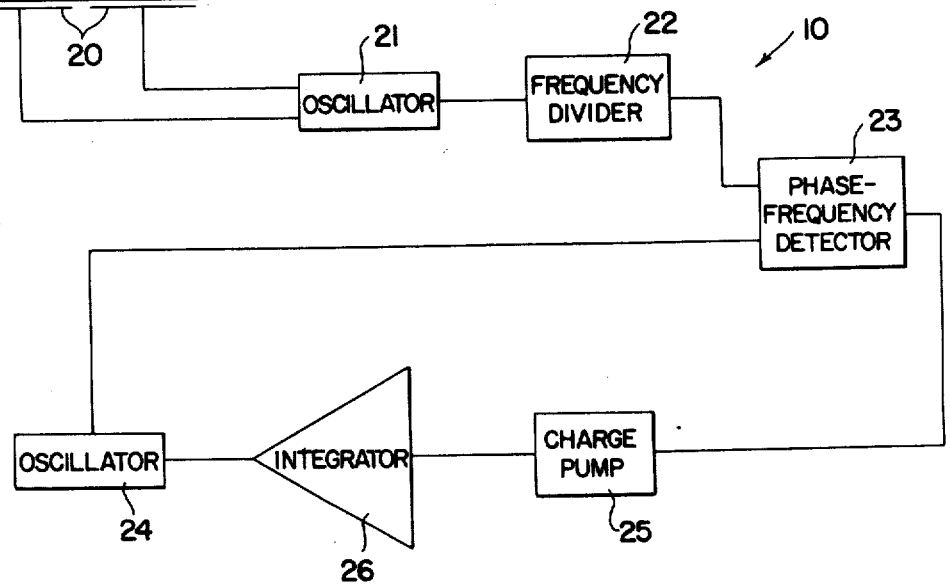
FIG. 2 is a block diagram showing a portion of the apparatus of the present invention, in particular, that portion which detects emboli, and which balances the circuit in the event of a change in the basic impedance of the fluid.

The details of the embolism monitoring and detecting apparatus 10 are shown in FIGS. 2 and 3. Afferent tube 13 is shown in FIG. 2 as carrying blood, saline or some other fluid. A plurality of electrodes 20 encircle tubing 13 to monitor the combined impedance effect of the tubing and the fluid. Electrodes 20 are connected to an oscillator 21 which is a low voltage very high frequency voltage controlled oscillator. The control voltage thereof is held constant thereby rendering oscillator 21 a variable frequency oscillator. In a typical situation when monitoring blood, the output signal of oscillator 21 would be a square wave having a frequency in the range of eight megahertz. Such high frequency is desirable to provide a high degree of sensitivity to the presence of an air bubble or other emboli in the blood stream which would cause an impedance change therein.

The output of oscillator 21 is fed to a conventional frequency divider 22 which is actually a bank of frequency dividers which divide the eight megahertz signal by a factor of $2^{13}$ to bring the signal down to a frequency compatible with the other components in the system. As will hereinafter be described, divider 22 is also utilized to obtain a plurality of frequency signals for use in conjunction with circuitry shown in FIG. 3. Thus, a signal having a frequency of approximately 967 hertz is fed to a phase-frequency detector 23 which is a conventional item such as manufactured by Motorola, Inc., Chicago, Illinois, Model No. MC4044.

Another voltage controlled oscillator 24 can be similar to oscillator 21 except that the impedance thereto is fixed so that the frequency of its output signal is dependent on the voltage fed thereto. Oscillator 24 is located in a feedback loop of phase-frequency detector 23, which loop includes a charge pump 25 and integrator 26. The output frequency of divider 22 and oscillator 24 is compared by detector 23 which puts out an output signal having a pulse or set of pulses, the duration of which is indicative of the size of the difference between the frequency outputs of divider 22 and oscillator 24. When there is no difference that signal will, of course, be zero. But when there is a difference, that signal is fed to charge pump 25 which is actually part of the Motorola MC4044 detector 23. Charge pump 25 includes a plurality of logic gates designed to indicate when the phase detector 23 indicates that the two inputs thereto are out of phase and which input is leading the other. Thus, the output of charge pump 25 is a positive or negative signal dependent on whether the output of divider 22 is leading or lagging the output of oscillator 24. The output of charge pump 25 is fed to integrator 26, a conventional item the output of which is a signal that is the time integral of the input thereto. Integrator 26 has a large capacitor, in excess of 200 microfarads, in its feedback loop to slow its response time to a rate on the order of one volt per ten seconds. Thus, if the outputs of divider 22 and oscillator 24 are in phase, there will be no signal out of detector 23 and the output of integrator 26 will remain substantially constant.

That which has just been described, that is, where the outputs of divider 22 and oscillator 24 are matched, can be called the balanced condition of the apparatus 10. Now if for some reason the basic impedance to oscillator 21 would change, for example, as by the introduction of saline into tubing 13 or by having changed the size of electrodes 20, the following operation would occur. Assume, for example, that starting from the balanced condition with the output signal of divider 22 and oscillator 24 being a 976 hertz signal as shown in graph B of FIG. 4, if saline were introduced into tubing 13 to purge the same or to force the remaining blood in the line into the patient, oscillator 21 would note the change in impedance and put out, for example, an 8.5 megahertz signal. While as a practical matter, this would be a slow change permitting oscillator 24 to track oscillator 21 very closely, for purposes of explanation herein, it can be assumed that it would be a sudden change. The output of frequency divider 22, shown as the A signal in FIG. 4, would then be on the order of 1037 hertz. Detector 23 will then begin to put out a signal, shown as waveform C in FIG. 4. It should be noted that while waveforms A and B of FIG. 4 are time coordinated, the remaining waveforms are not necessarily time coordinated with A or B, or with each other, but rather merely depict what a particular signal could be out of a particular device.

In any event, the C signal, which started at a balanced zero condition, first exhibits a pulse of some width, for example 30 microseconds, indicative of the 61 hertz difference in frequency. This pulse would cause the integrator to slowly create the ramp signal D which is the error voltage signal that increases the frequency of oscillator 24. As that frequency increases, the output pulses of the phase detector 23 become of shorter duration until a balance or zero signal is reached again. The above-described occurrence will most typically happen when the apparatus is first turned on because oscillator 21 will immediately put out a frequency signal proportional to the impedance and oscillator 24 will track it at a slow rate and will match oscillator 21 in, for example, about fifteen seconds due to the size of the capacitor in integrator 26 as previously described.

Once this balanced condition is reached, the apparatus is ready to monitor the fluid to detect the presence of an air bubble or embolism therein. If an air bubble were to pass the electrodes 20, the output of oscillator 21 could appear as waveform E of FIG. 4. The first pulse of waveform E is indicative of the normal balanced frequency. Then as the bubble passes, the frequency increases to a maximum, indicated by the third and fourth pulses of short duration, and then the frequency begins to decrease again until it is back to normal as indicated by the last pluse of waveform E. Because this happens fairly fast, dependent on the speed at which the bubble passes electrodes 20, oscillator 24 cannot follow it but rather continues to put out a waveform, waveform F in FIG. 4, proportional to the impedance of the tubing and the fluid, that is, the balanced condition. A typical output of phase-frequency detector 23 for this condition is shown as waveform G of FIG. 4. Starting from the balanced or zero condition, the output G could first exhibit a spike-like like pulse and as the bubble passed the width of the pulses would increase to some maximum and then decrease again to eventually return to a zero condition when waveform E returned to its original frequency matching that of waveform F. Waveform G of detector 23 is then used to actuate the control circuitry best shown in FIG. 3.

The control circuit part of apparatus 10 includes operation in two modes, a set mode and a run mode, as determined by the position of a switching device generally indicated by the numeral 30. Switching device 30 includes a mechanical switch 31 which is shiftable from a set to a run position as shown in FIG. 3. When in the set position, a yellow light 32 glows indicative of such and an analog or bilateral switch 33 is turned on. Switch 33 is a conventional device such as can be purchased from Motorola, Inc., Chicago, Illinois, Model MC14016. The turning on of switch 33 permits pulses from a conventional frequency divider 34 to be fed to a conventional up/down binary counter 35 and a decimal counter 36.

Frequency divider 34 receives its signal from either a fast count switch 38 or a slow count switch 39. Switches 38 and 39 are connected to frequency divider 22 (FIG. 2). The connection is such that the signals to switches 38 and 39 are not at the same frequency as that fed to phase-frequency detector 23. Rather, intermediate frequency signals are tapped off of divider 22, one at a faster frequency than the other (in actual practice some thirty times faster) for reasons to hereinafter become evident. Typical outputs of divider 34 are 60 hertz and 2 hertz upon depressing switches 38 and 39, respectively.

It is the prime function of the set mode to preselect an alarm limit or level into the system, the purpose of which will hereinafter become evident. If that alarm limit is to be 150 pulses, for example, the fast count switch is depressed which sends pulses at 60 hertz to decimal counter 36 and up/down binary counter 35 which is counting up at this time. This count is stored in the counters and displayed in a conventional light-emitting-diode (LED) display 40 that is driven by a driver included in the counter 36. As the 150 count is approached the slow count switch 39 is depressed so that the desired alarm level can be precisely entered in the counters.

With the preselected alarm level being entered in counters 35 and 36, the mechanical switch 31 is shifted to the run position. This accomplishes a number of functions: the yellow light 32 goes out and the green light 41 comes on; the decimal counter 36 and LED display 40 are reset to zero; the up/down binary counter is shifted to a down mode while the preselected alarm level remains stored therein; and a second bilateral switch 42, similar to switch 33, is turned on while switch 33 is turned off. As such, the input to the counters 35 and 36 is from a one-shot multivibrator 43 rather than frequency divider 34.

A conventional decimal counter 44 receives two inputs, one from the phase-frequency detector 23 and the other from the frequency divider 22. As has been previously described, the input from phase-frequency detector is a series of pulses, the width of which is dependent on the size of the air bubble with a typical waveform being plot G of FIG. 4. The input from frequency divider 22 can be selected at a higher frequency than that provided to detector 23. For example, a frequency of 8 megahertz divided by $2^6$ can be tapped off of divider 22 and used as this input to counter 44.

The input to decimal counter 44 from detector 23 tells the counter when to start and stop counting. Referring to waveform G, counter 44 will start counting on the downward transition of each pulse and stop counting on the upward transition of each pulse. The input to counter 44 from divider 22 acts as a clock input presenting the count to increment the counter only when permitted to do so by the G waveform.

Decimal counter 44 is selected to have ten discrete outputs 1 through 10. The apparatus of FIG. 3 is shown as being operable on two of these outputs. If the output of phase detector 23 is a pulse of long enough duration to permit the counter 44 to count ten pulses from frequency divider 22, this is indicative of a large air embolism passing by electrodes 20 on the order of 0.25 milliliters. Such an embolism could prove harmful to the patient and as such, immediate measures must be taken. Thus, if the ten count is reached, a signal is sent through an OR gate 45 to provide an actuation signal for an alarm circuit. The sensitivity for detecting these large emboli is controlled by the frequency of the clock pulse from divider 22 and the count which counter 44 is permitted to reach before the signal is sent to OR gate 45. Thus, with a clock pulse of eight megahertz divided by $2^6$ and by selecting ten as the desired limit of the counter, an embolism on the order of 0.25 milliliters can be detected. While any type of alarming device could be utilized, and thus no specific alarm has been shown, it should be evident to one skilled in the art that an audio and/or visual alarm could be sounded or more important, the actuation signal could automatically stop the pump in unit 11 or clamp the hose 13 to prevent the embolism from reaching the patient.

If the embolism is not large enough to permit counter 44 to reach the ten level, the smaller embolism in and of itself should not be damaging to the patient. But an accumulation of smaller emboli could well prove detrimental. Thus, the control circuit of FIG. 3 includes an accumulation circuit consisting primarily of multivibrator 43, counter 35 and OR gate 45. The second output of decimal counter 44 provides a triggering signal to multivibrator 43. Although this output could be selected as any one of the nine remaining outputs of counter 44, the output upon reaching the count of two is preferred. By triggering the multivibrator every time the counter 44 reaches the two level as opposed, for example, to the one level, false readings which might occur from noise and the like that would increment the counter to the one level, are avoided, yet each time the phase detector output has a pulse of a long enough duration to permit the counter 44 to receive two pulses from frequency divider 22, indicative of a small embolism, the multivibrator is triggered continually until the counter is cleared which, as previously described, occurs on the up transition of a pulse out of the phase detector 23. Thus, the sensitivity of the accumulation circuit is based on the selection of the clock frequency from divider 22 to counter 44, the selection of the count needed to trigger the multivibrator 43, and the time constant of the multivibrator itself. It has been found that using a clock frequency of eight megahertz divided by $2^6$, permitting counter 44 to count to two, and using a multivibrator having a time constant on the order of 5.2 milliseconds, a twenty microliter embolism will trigger the multivibrator one time. If the count of counter stays at two or above long enough for the multivibrator to trigger more than once, indicative of an embolism larger than 20 microliters, it will continue to provide output pulses until the counter goes below two. When the multivibrator is triggering, both the green light 46 and the yellow light 47 are on. When the multivibrator is not triggering, only green light 46 will be on.

These outputs of multivibrator 43 increment the decimal counter 36 which in turn drives the LED display 40 so that a visual monitoring of the accumulation of emboli can be obtained. In addition, the up/down binary counter 35 is incremented downwardly from the alarm level which had been set into the counter when switch 30 was in the set mode, in the example, 150. When counter 35 reaches zero, it sends a signal through OR gate 45 to provide an actuation signal for an alarm circuit previously described.

It should thus be evident that the apparatus of the present invention and method of operation thereof permits one to monitor extracorporeal circulation of a fluid to detect emboli therein to immediately take remedial measures should an embolism of a predetermined size or volume be present and to take such measures when a predetermined quantity of smaller emboli are accumulated, all without false alarms should the basic impedance of the fluid change due to a cause not associated with the presence of an embolism, thus substantially improving the extracorporeal circulation art.

I claim:

1. Apparatus for detecting at least one embolism contained in a fluid during extracorporeal circulation of the fluid in a tubing comprising:
    means to monitor the electrical impedance of the tubing, fluid and any emboli contained therein having an output signal whose voltage is proportional to the electrical impedance of the tubing, fluid and any emboli contained therein,
    first oscillator means receiving the output signal from said means to monitor and providing at least one output signal whose frequency is proportional to the electrical impedance of the tubing, fluid and any emboli contained therein,
    second oscillator means having an output signal whose frequency is proportional to the electrical impedance of the fluid and tubing,
    detector means receiving the output signals from said first and second oscillator means and providing an output signal the duration of which is indicative of the difference between the frequencies of the output signals of said first and second oscillator means,
    said detector means having an electrical feedback loop, said second oscillator means being in said feedback loop, integrator means in said feedback loop and proviging an output signal which is the time integral of the input thereto, said integrator means receiving the output signal of said detector means and providing said output signal to said second oscillator means, the output of said second oscillator means being fed back to said detector means to complete the feedback loop, and
    control means for providing an actuation signal indicative of the presence of at least one embolism including
        counter means receiving the output signal of said detector means and a frequency signal of said first oscillator means and providing a plurality of output signals, said frequency signal incrementing said counter means only when said counter means receives a signal from said detector means, accumulation circuit means including multivibrator means receiving a first signal of said counter means and providing a periodic output signal as long as it is receiving the first output signal, and second counter means having a predetermined accumulation of emboli stored therein and counting each periodic signal from said multivibrator means to provide an output signal when said predetermined accumulation is reached, and gate means receiving the output signal of said second counter means and a second signal from said counter means being indicative of the presence of a single embolism of predetermined size, said gate means providing the actuation signal.

2. Apparatus according to claim 1, wherein said accumulation circuit means further includes third counter means receiving the periodic output signal from said multivibrator means and providing an output signal indicative of the accumulation of emboli, and display means receiving the output of said third counter means and visually displaying the same.

3. Apparatus for detecting at least one embolism contained in a fluid during extracorporeal circulation of the fluid in a tubing comprising:

means to monitor the electrical impedance of the tubing, fluid and any emboli contained therein having an output signal whose voltage is proportional to the electrical impedance of the tubing, fluid and any emboli contained therein, first oscillator means receiving the output signal from said means to monitor and providing at least one output signal whose frequency is proportional to the electrical impedance of the tubing, fluid and any emboli contained therein, second oscillator means having an output signal whose frequency is proportional to the electrical impedance of the fluid and tubing, detector means receiving the output signals from said first and second oscillator means and providing an output signal the duration of which is indicative of the difference between the frequencies of the output signals of said first and second oscillator means, said detector means having an electrical feedback loop, said second oscillator means being in said feedback loop, integrator means in said feedback loop and providing an output signal which is the time integral of the input thereto, said integrator means receiving the output signal of said detector means and providing said output signal to said second oscillator means, said integrator means having a time constant, the output of said second oscillator means being fed back to said detector means to complete the feedback loop, and control means for providing an actuation signal indicative of the presence of at least one embolism including counter means receiving the output signal of said detector means, said counter means being incremented when receiving the output of said detector means and providing an output signal indicative of said incrementation, and multivibrator means receiving the output signal of said counter means, said multivibrator means having a time constant substantially less then the time constant of said integrator means.

4. Apparatus for detecting at least one embolism contained in a fluid during extracorporeal circulation of the fluid in a tubing comprising:

means to monitor the electrical impedance of the tubing, fluid and any emboli contained therein having an output signal whose voltage is proportional to the electrical impedance of the tubing, fluid and any emboli contained therein, first oscillator means receiving the output signal from said means to monitor and providing at least one output signal whose frequency is proportional to the electrical impedance of the tubing, fluid and any emboli contained therein, second oscillator means having an output signal whose frequency is proportional to the electrical impedance of the fluid and tubing, detector means receiving the output signals from said first and second oscillator means and providing an output signal the duration of which is indicative of the difference between the frequencies of the output signals of said first and second oscillator means, and control means receiving the output signal of said detector means and providing a plurality of output signals including an actuation signal indicative of the presence of at least one embolism, said control means including counter means and accumulation circuit means, said counter means receiving an output signal of said detector means and a frequency signal of said first oscillator means, said frequency signal incrementing said counter means only when said counter means receives a signal from said detector means, said accumulation circuit means including multivibrator means receiving a first signal of said counter means and providing a periodic output signal as long as it is receiving the first output signal, and second counter means having a predetermined accumulation of emboli stored therein and counting each periodic signal from said multivibrator means to provide an output signal when said predetermined accumulation is reached indicative of said predetermined accumulation, said counter means providing a second signal being indicative of the presence of a single embolism of predetermined size, and gate means receiving the output signal of said second counter means and said second signal from said counter means and selectively providing the actuation signal.

5. Apparatus according to claim 4, said control means further including means to select the predetermined accumulation of emboli.

6. Apparatus according to claim 4, wherein said accumulation circuit means further includes third counter means receiving the periodic output signal from said multivibrator means and providing an output signal indicative of the accumulation of emboli, and display means receiving the output of said third counter means and visually displaying the same.

7. Apparatus for detecting at least one embolism contained in a fluid during extracorporeal circulation of the fluid in a tubing comprising:

means to monitor the electrical impedance of the tubing, fluid and any emboli contained therein having an output signal whose voltage is proportional to the electrical impedance of the tubing, fluid and any emboli contained therein, first oscillator means receiving the output signal from said means to monitor and providing at least one output signal whose frequency is proportional to the electrical impedance of the tubing, fluid and any emboli contained therein, second oscillator means having an output signal whose frequency is proportional to the electrical impedance of the fluid and tubing, detector means receiving the output signals from said first and second oscillator means and providing an output signal the duration of which is indicative of the difference between the frequencies of the output signals of said first and second oscillator means, integrator means receiving the output of said detector means and providing and output which is the time integral of its input, said second oscillator means receiving the output of said integrator means, said integrator means having a time constant, control means for providing a plurality of output signals including an actuation signal indicative of the presence of at least one embolism, said control means including counter means receiving the output signal of said detector means and a frequency signal of said first oscillator means, said frequency signal incrementing said counter means only when said counter means receives a signal from said detector means, and providing a plurality of output signals including a first output signal indicative of the presence of at least one embolism, accumulation circuit means for providing an output signal indicative of a predetermined accumulation of emboli including multivibrator means receiving a second signal of said counter means, said multivibrator means having a time constant substantially less then the time constant of said integrator means, and gate means receiving the output signal of said accumulation circuit means and said first signal from said counter means and selectively providing said actuation signal.

* * * * *